United States Patent [19]
Novello et al.

[11] Patent Number: 5,626,819
[45] Date of Patent: May 6, 1997

[54] BLOOD OXYGENATORS

[75] Inventors: Waldyr P. Novello, Campinas; Mario Drummond; Adolfo A. Leirner, both of São Paulo, all of Brazil

[73] Assignee: Fundação E. J. Zerbini, Sao Paulo - SP, Brazil

[21] Appl. No.: 507,749

[22] Filed: Jul. 26, 1995

[51] Int. Cl.[6] ............... A61M 1/14; A61M 1/34
[52] U.S. Cl. .................. 422/45; 422/48; 261/92; 261/DIG. 28
[58] Field of Search ............ 422/45, 48; 261/92, 261/87, DIG. 28

[56] References Cited

U.S. PATENT DOCUMENTS

| | | | |
|---|---|---|---|
| 3,034,505 | 5/1962 | Sobol | 422/45 |
| 3,053,254 | 9/1962 | Galajda, Jr. | 261/92 |
| 3,211,148 | 10/1965 | Galajda, Jr. | 261/92 |
| 3,413,095 | 11/1968 | Bramson | 422/45 |
| 3,977,976 | 8/1976 | Spaan et al. | 422/48 |
| 4,212,741 | 7/1980 | Bromfield | 210/241 |
| 5,026,650 | 6/1991 | Schwarz et al. | 435/286 |

FOREIGN PATENT DOCUMENTS

| | | |
|---|---|---|
| 9305166 | 10/1995 | Brazil. |
| 2434262 | 1/1976 | Germany. |
| 1421441 | 1/1976 | United Kingdom. |

*Primary Examiner*—Nina Bhat
*Attorney, Agent, or Firm*—Darby & Darby

[57] ABSTRACT

Provided is an improved disk oxygenator having a hollow median longitudinal shaft with a plurality of orifices to allow oxygen to be diffused radially through a cylindrical reservoir. Also provided is a disk oxygenator with a hollow longitudinal shaft comprised of a series of disks. The disks are provided with a central annular cylindrical passageway.

11 Claims, 3 Drawing Sheets

BLOOD OXYGENATORS

FIELD OF THE INVENTION

This invention relates to blood oxygenators. More specifically, this invention relates to improvements in disk oxygenators. The invention provides a axial and central source of oxygen through a hollow median longitudinal shaft or passageway having a plurality of slits or orifices such that oxygen is introduced into a reservoir through the slits or orifices.

BACKGROUND OF THE INVENTION

Oxygenators are used to oxygenate the blood of patients during surgical procedures. This is accomplished during the extra-corporal circulation of the blood. The oxygenators typically used are in the art are of various types and can be generally classified as blood film oxygenators and membrane oxygenators. Typical apparatus used by workers are cylinder oxygenators, network oxygenators, bubble oxygenators and disk oxygenators.

Disk oxygenators have been known since the 1950's and are based on the same functional principles as the older type cylinder oxygenators. These disk oxygenators are made up of a large glass blood reservoir in the shape of a tubular cylinder. The reservoir is closed by caps which are positioned horizontally at both ends of the reservoir. The reservoir is crossed through its longitudinal and median axis by a shaft, turned by an appropriate motor, metal disks having ridges or corrugations on both sides being arranged around the shaft. These disks provide a greater surface area on which to expose the blood to oxygen than is provided by cylinder type apparatus. During use of the standard equipment, the blood enters the inside of the reservoir through a lower inlet. Heat exchangers are also used to control the temperature of the blood flowing into the reservoir. In this process, the blood occupies approximately one-third of the inner volume of the reservoir. A horizonal tube is also provided in the upper inner part of the reservoir which crosses the; reservoir longitudinally and has a number of orifices through which the oxygen is introduced into the reservoir.

Once the inner shaft of the oxygenator begins to turn, along with the inner metallic disks which are partially submerged in the blood, the drag action of the attached disks causes the surfaces of the disks to pick up a film of blood. The blood is then carried by the disks to the upper part of the reservoir where a blood/oxygen contact occurs resulting in the oxygenation of the blood. Once the blood has been oxygenated, it leaves the reservoir and is returned to the patient.

However, there are several drawbacks in the use of this equipment. Because the equipment must be thoroughly cleaned and sterilized after each use to avoid the risk that the equipment may be contaminated with blood-borne pathogens that could be transferred from one surgical operation to the next, the cleaning process used between surgeries is time-consuming and complex, resulting in significant equipment down-time after each use.

Another drawback is that the equipment is relatively large in size, which results in a large quantity of blood being stored in the reservoir during surgery. Moreover, the disk oxygenator functions as a centrifugal pump which tends to keep the oxygen away from the middle of the disks. Thus, the blood is not always wholly or uniformly oxygenated because the blood closest to the shaft receives less oxygen.

A further drawback to using the conventional disk oxygenators is that a very elaborate system is needed to control the level of blood inside the reservoir. An elaborate system is also needed to recapture the blood remaining at the end of the surgery.

Thus, an object of the present invention is to provide an improved disk oxygenator which essentially eliminates the risk of contamination from one surgical procedure to the next surgical procedure. It is also an object of the present invention to reduce or eliminate the extensive labor needed to assemble and disassemble the equipment in order to clean and sterilize the disk oxygenation equipment after surgery. It is a further object of the present invention to provide a blood oxygenator that is smaller in size so that less blood is stored inside the reservoir during surgery. Still further objects of the invention include greater gas transfer control, easier control of the blood level inside the oxygenator and easier recapture of the blood remaining at the end of surgery.

SUMMARY OF THE INVENTION

Figure 1:
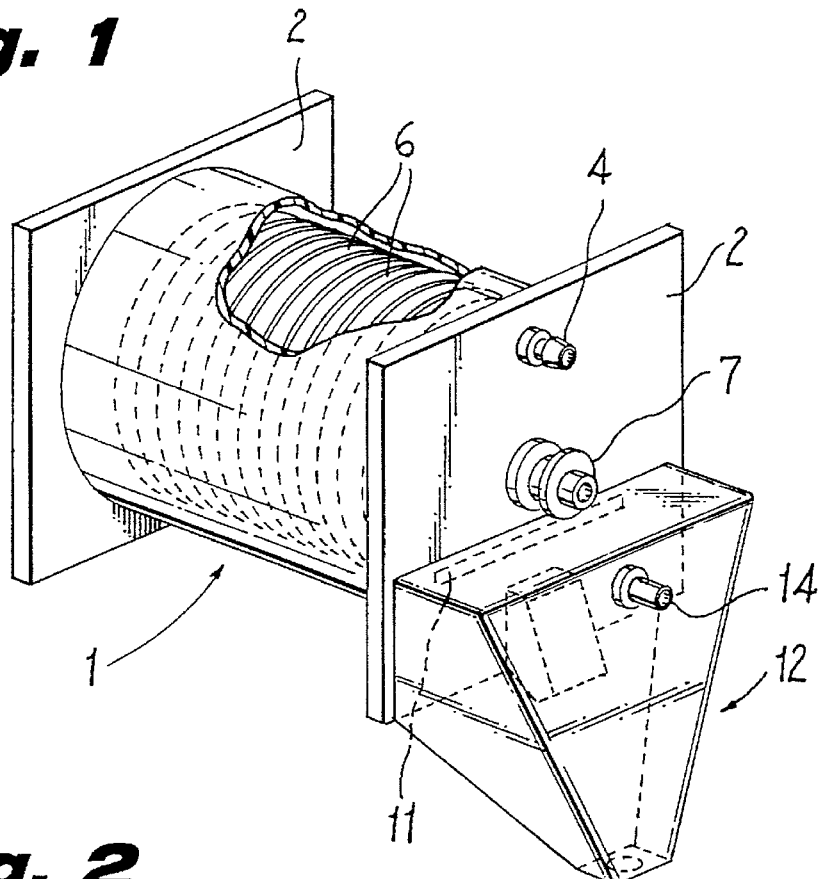
FIG. 1 is a perspective view of a disk oxygenator encompassed by the present invention.
Figure 2:
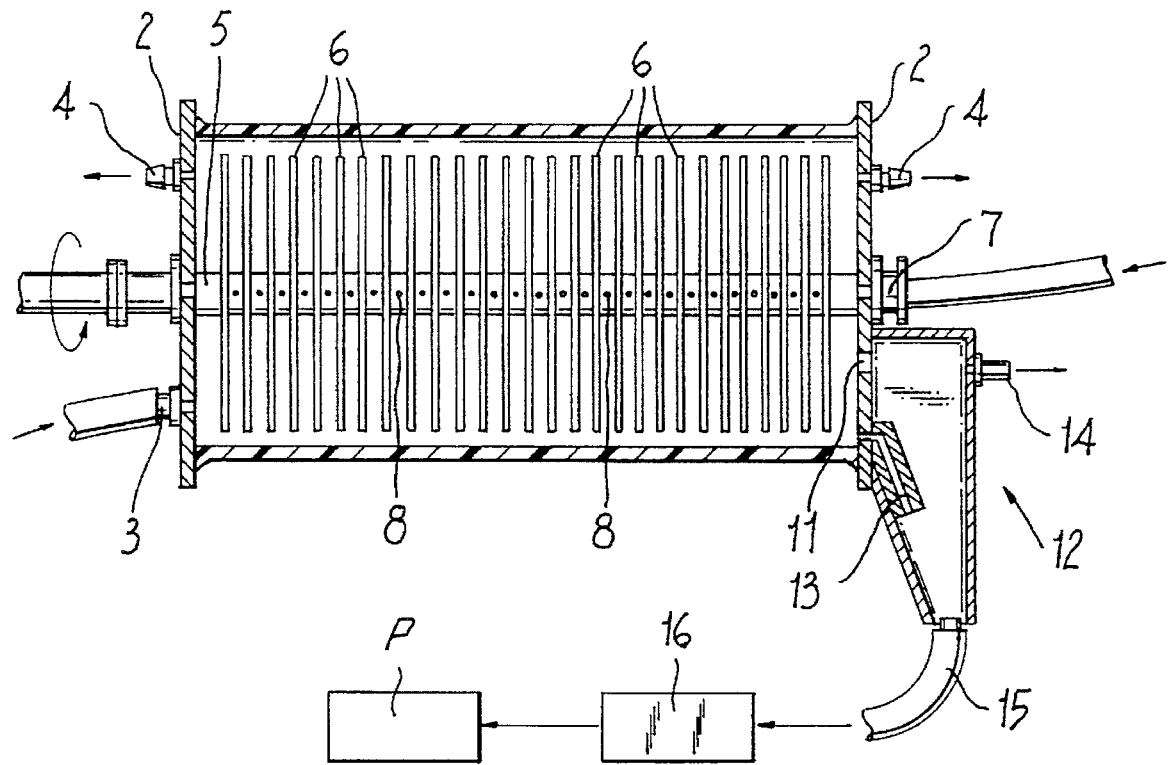
FIG. 2 is a diagrammatic cross-sectional view of a disk oxygenator encompassed by the present invention.

The invention comprises a blood oxygenator with a cylindrically shaped reservoir located horizontally. Two ends are provided on the reservoir and are closed by caps. One cap has a lower blood inlet and an upper outlet. Both caps may also contain an upper gas outlet. The reservoir has a hollow, substantially median shaft attached longitudinally to the ends of the reservoir. The shaft includes a plurality of orifices and an oxygen providing means, attached to an end of the shaft, to allow oxygen to enter the shaft, axially and centrally, and to be diffused radially through the orifices and into the reservoir. These orifices or slits may be graduated in width increasing in size starting from the beginning of the shaft (where the oxygen enters the shaft). The orifices or slits may also match the spaces located between the disks. Attached to the shaft are a plurality of disks arranged radially about the shaft. A means for rotating the shaft about its longitudinal axis is also provided.

According to the present invention, the upper oxygen distribution tube of conventional oxygenators is eliminated, and the oxygen distribution system is moved to the center of the oxygenator where the oxygen is provided centrally and radially.

One of the caps also has a horizontal slit situated transverse to the reservoir. An oxygenated blood reservoir annex is then provided and can be attached to the reservoir; it is suitable for allowing oxygenated blood to be collected. The horizontal slit constitutes a blood level control element inside the oxygenator and coincides with a low part of the reservoir. A low drainage tube is provided and is attached to the reservoir allowing the blood to be emptied into the reservoir annex. The reservoir annex is further provided with an upper opening for the discharge of gas and with a lower tube connected to a pump.

DETAILED DESCRIPTION OF THE INVENTION

In the present invention, the median longitudinal shaft is hollow and provided with a plurality of oxygen infusion or injection orifices. Preferably, the shaft is provided with a plurality of slits of gradually increasing width starting at the beginning of the shaft where the oxygen enters and increasing in width toward the end of the shaft. The oxygen flows (after infusion or injection) axially through the inside of the shaft and is then diffused radially through the slits and into a blood chamber reservoir.

In another aspect of the invention, the separate median longitudinal shaft is eliminated, and each of the inner disks are themselves provided with a central annular segment collectively providing a passageway through which oxygen is introduced.

A superior benefit of this invention over prior oxygenators is that when the disks turn, the oxygen is distributed from the median shaft or passageway toward the edges of the disks radially, favoring the centrifugal movement of the gas. This movement creates a uniform distribution of the oxygen, not only along the central shaft, but also along the edges of the disks, resulting in a more homogenous oxygenation.

The disks can be made of metal or a thermoplastic material. The disks may be made of porous or nonporous material and may also be texturized or non-texturized. They can also be in the shape of a screen or, as an option, the disks can be hollow.

In a preferred embodiment, when the disks are made of two or more porous blades, the film of blood retained on the surface of the disks is able to receive oxygen inside as well as outside the disks. That is, oxygen is provided in the space formed between the two blades of each disk as well as in the space formed between two adjacent disks so that the blood is oxygenated in a uniform manner throughout the thickness of the film.

Due to this improved performance, the necessary number of disks is reduced and a more compact assembly is achieved, making the dimensions of the oxygenator substantially smaller then those provided in the prior art. Moreover, since the conventional upper oxygen distribution tube of standard disk oxygenators has been eliminated, it is also possible to achieve a reduction in the diameter of the reservoir and, consequently, the inner volume. This reduction in the inner volume of the reservoir substantially reduces the quantity of blood inside the oxygenator during surgical procedures.

Preferably, the disks are disposable. This feature eliminates the need for the disks to be assembled and disassembled for cleaning, and results in savings of time and labor. This feature also reduces the risk that the equipment will be contaminated from one surgery to the next. Also, since much of the device of this invention is disposable, it is possible to comply with the more modern trend of using disposable surgical materials in cardiac surgery, therefore placing it on a level, in economic terms, with the bubble oxygenator and the disposable membrane apparatus currently in use.

The improved oxygenator may also include a blood level control element provided in the reservoir caps. A preferred example of a blood level control element is a horizontal slit that is transverse in relation to the reservoir. This control element allows blood to be emptied into a blood reservoir annex. During use, this blood reservoir annex is oxygenated. The slit acts to keep the inner blood level in the oxygenator constant without the need for a more sophisticated control device. Since the level of blood is maintained constant inside the oxygenator, the risk of creating air bubbles is reduced or avoided. Also avoided is hemolysis, which occurs when low blood levels cause the peripheral edges of the disks to come into contact with the surface of the blood. Over-filling the reservoir is also avoided. Hence, the improved device results in a stable oxygenation process where the blood levels do not vary.

Further provided is a low drainage (drip) tube, capable of recapturing all of the oxygenated blood at the end of each surgery. This tube is located very near the lower part of the reservoir, and also leads to the reservoir annex for already oxygenated blood.

The oxygenator may also incorporate a heat exchanger for controlling the blood temperature.

FIGS. 1–5 illustrate preferred embodiments of the invention. In a preferred embodiment of the present invention the oxygenator comprises a blood reservoir (1), of small dimensions, formed of appropriate thermo-plastic material and having a tubular cylindrical shape which is located horizontally. The ends of the reservoir are closed by caps (2) composed of appropriate thermo-plastic material. A first cap is provided with a lower blood inlet (3) through which the patient's blood is introduced into the oxygenator. Both caps (2) are provided with upper outlets (4) for the release of oxygen and other gases. Reservoir (1) is provided longitudinally with a median shaft (5) which can be turned by activating an appropriate motor and around which are placed disks (6) made of metal or an appropriate thermo-plastic. The disks (6) can be porous or non-porous, texturized or non-texturized, and may be in the shape of a screen.

Oxygen inlet (7) inside the reservoir (1) is shown centrally and axially located. Longitudinal median shaft 5 is hollow and provided with a number of orifices (8) which coincide with the spaces between the disks (6) (see FIG. 3). Oxygen is injected or infused centrally and axially through the oxygen inlet. Preferably, slits (8') are provided in the longitudinal median shaft (5), the slits also matching the spaces between the disks (6), and are presented in graduated widths starting from the beginning of the shaft where the oxygen enters toward the end of the shaft (see FIG. 4). In this way, the oxygen, which enters centrally and axially through the inside of the longitudinal shaft (5) and exits through the orifices (8) or, preferably, slits (8'), is radially distributed from the median shaft toward the edges of the disks. This causes the centrifugal movement of the gas resulting in a more uniform distribution of the oxygen on the shaft (5) as well as on the edges of the disks (6). When slits (8') are used, the distribution of oxygen is even more uniform along the whole length of the shaft (5) due to the graduated widths of the slits, starting from the beginning of the shaft where the slits are smaller, becoming larger toward the end. This arrangement of slits eliminates the risk of having a greater concentration of oxygen at the beginning of the shaft and a smaller concentration of oxygen at the end of the shaft.

Figure 3A:
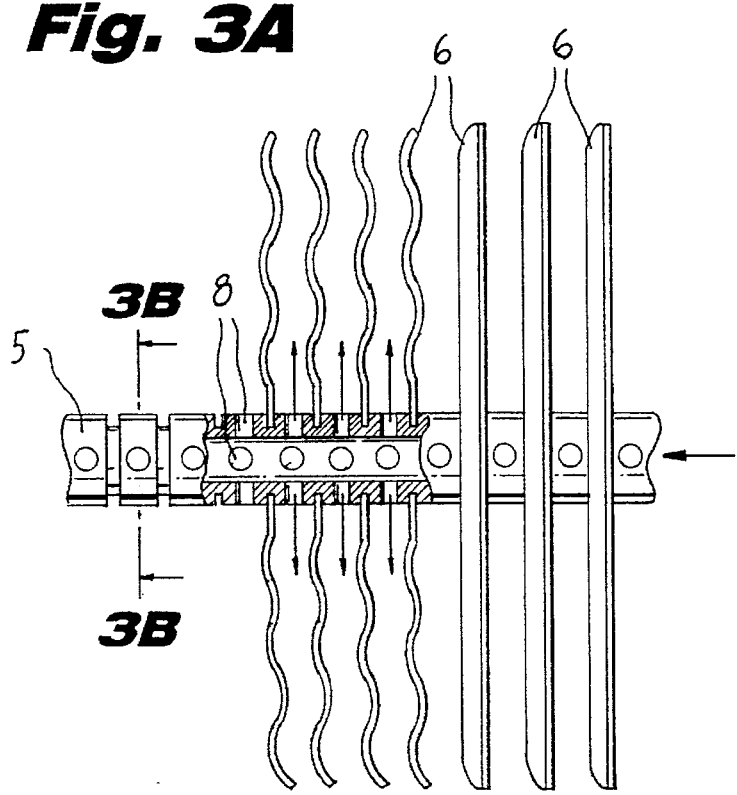
FIG. 3A is an elevated view, partly in section, of disks attached to a hollow longitudinal shaft containing oxygen diffusing orifices.
Figure 3B:
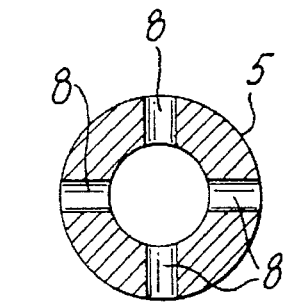
FIG. 3B is a cross-sectional view along the line 3B—3B of FIG. 3A.
Figure 4A:
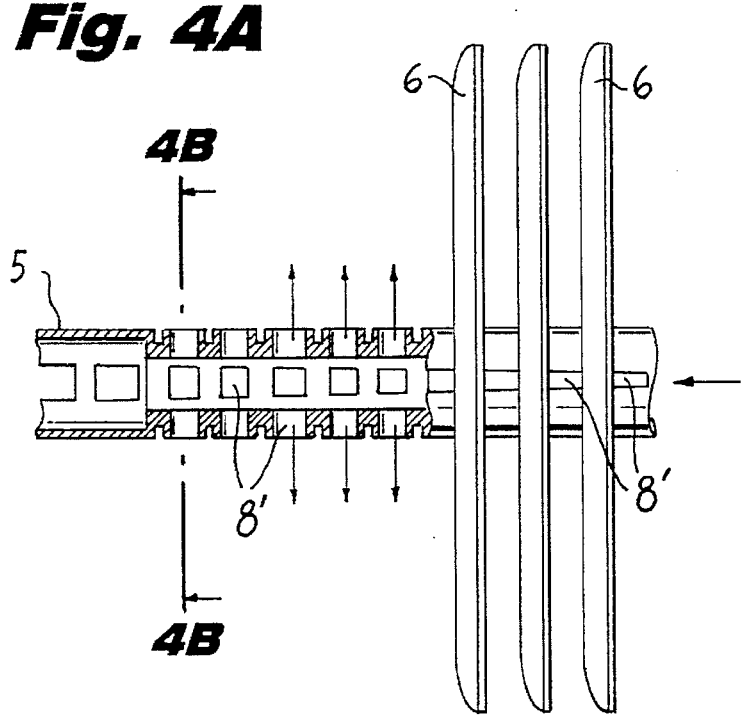
FIG. 4A is an elevated view, partly in section, of disks attached to a hollow longitudinal shaft containing slits of increasing size.
Figure 4B:
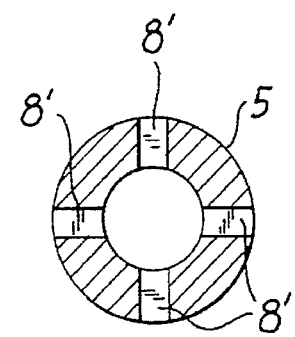
FIG. 4B is a cross-sectional view along the line 4B—4B of FIG. 4A.
Figure 5:
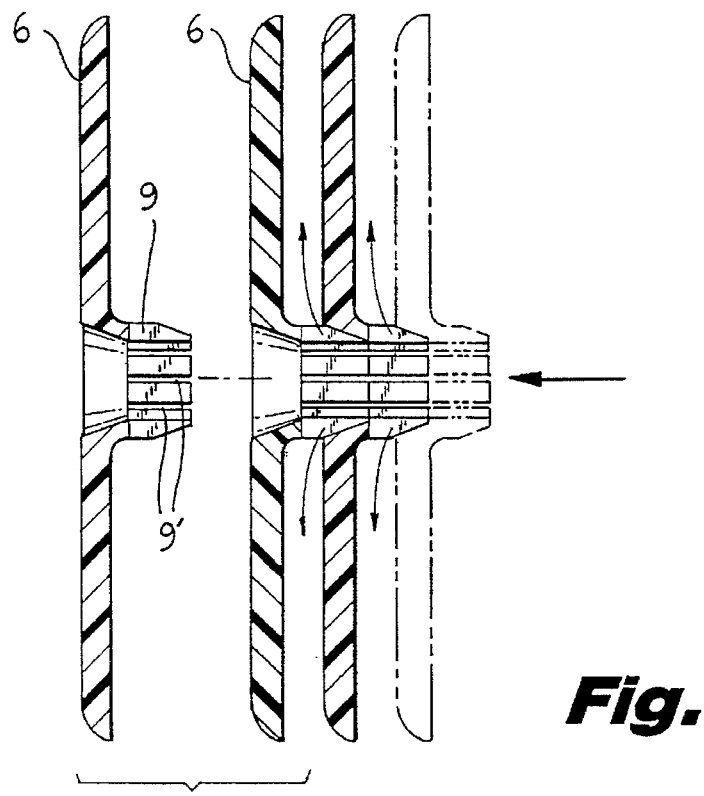
FIG. 5 is an elevated view, partly in section, of disks attached with central winged annular elements.

The disks (6) of FIG. 3 are made of metal and are provided with corrugated ridges. In other embodiments of the present invention, as presented in FIGS. 5 and 6, the separate longitudinal median shaft (5) is eliminated and the disks (6) are provided with a cylindrical annular central segment (9), preferably winged (9'), and more preferably provided with orifices (9"), which can be fitted and affixed to a segment of the adjacent disks. Segments (9) are fitted together to form or delimit a hollow median longitudinal central passageway which is capable of turning and through which oxygen is provided. Oxygen enters centrally and axially inside the passageway formed by the annular segments (9) of disks (6), passes by the wings (9') or orifices (9"), and is distributed from the passageway toward the edges of the disks radially, thereby causing a more uniform distribution of oxygen.

Figure 6:
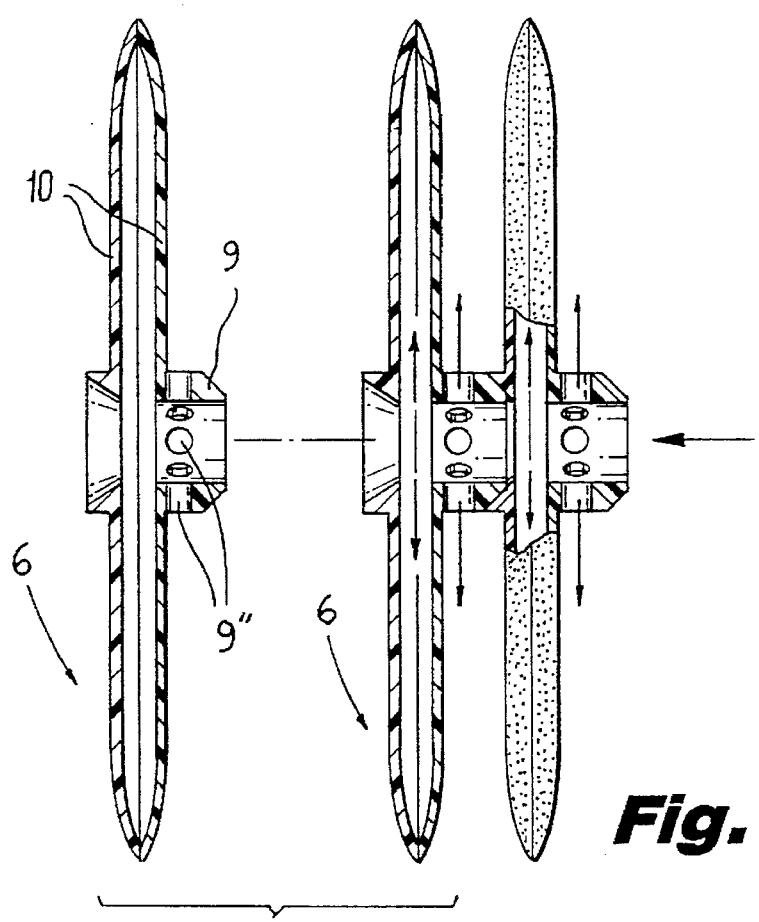
FIG. 6 is an elevated view, partly in section, of disks made of two blades.

In FIG. 6, the disks (6) shown are made of appropriate thermo-plastic material having a central winged annular segment. In FIG. 6 the disks are shown made of porous material, are hollow, and are preferably made of two blades (10). When the disks comprise at least two blades which are porous, the film of blood retained on the surfaces receive oxygen on the inside as well as on the outside, that is, in the space formed between the two blades (10) as well as on each disk (6) resulting in blood that is uniformly oxygenated.

In a preferred embodiment of the invention, one of the caps (2) has a horizontal slit (11) transverse in relation to the reservoir. This slit allows blood to be emptied into a reservoir annex (12). The annex may be of any appropriate size and shape and may even be incorporated into the reservoir. The reservoir annex is preferably used for oxygenated blood. During the operation of the oxygenator, the slit (11) will cause the internal blood level of the oxygenator to be maintained during the functioning of the equipment.

In cap (2), coinciding with the lowest part of reservoir (1), a low drainage tube (13) is provided. This tube allows blood to be emptied into the reservoir annex (12). This added feature also allows any blood remaining after surgery to be completely emptied from the main reservoir. Air outlet opening (14) located in the upper part of the reservoir annex (12) allows the inner chamber of the reservoir to be depressurized.

Further provided is a tube (15) shown leaving the lower part of the reservoir annex (12). During operation of the oxygenator, this tube carries the oxygenated blood to the conventional pump (16) and on to the patient (P).

In another aspect of the invention a heat exchanger (not shown) is provided which is incorporated into the oxygenator and is preferably incorporated into the body of the reservoir (1).

The above-described improved disk oxygenator results in a technically and functionally better disk oxygenator having many advantages, including: better performance; more compact size; smaller volume of blood inside the equipment; elimination of waste; elimination of assembly, disassembly and cleaning services; stable performance due to the permanent blood level control; ease of removing remaining blood following surgery; and low lesion indices of the blood constituents.

It is apparent that various modifications can be made without departing from the spirit and the scope of this invention.

What is claimed is:

1. A blood oxygenator comprising:

a. a horizontally disposed cylindrical reservoir having a first end and a second end;

a. a first cap, closing said first end, having a lower blood inlet and an upper gas outlet;

b. a second cap closing said second end;

c. a hollow median shaft attached to said caps, disposed longitudinally within said cylindrical reservoir, said shaft provided with a plurality of orifices;

d. an oxygen providing means attached to one end of said shaft to allow oxygen to enter said shaft axially and centrally and to be diffused radially through said orifices and into said reservoir;

e. a plurality of disks attached to said shaft; and f. a means for rotating said shaft about its longitudinal axis.

2. The blood oxygenator of claim 1 wherein said orifices are formed as slits.

3. The blood oxygenator of claim 2 wherein said slits are graduated in size from end to end, the smallest slit at the end of the shaft where the oxygen providing means is located.

4. The blood oxygenator of claim 1 wherein the disks are hollow and porous and comprise at least two blades.

5. The blood oxygenator of claim 1 wherein at least one of said caps is provided with blood level control means.

6. The blood oxygenator of claim 5 wherein said blood level control means is a horizontal slit formed near the bottom of said cap.

7. The blood oxygenator of claim 5 further including a blood reservoir annex in fluid connection with said blood level control means.

8. A blood oxygenator comprising:

a) a horizontally disposed cylindrical reservoir having a first end and a second end;

b) a first cap having a lower blood inlet and an upper gas outlet, closing said first end;

c) a second cap closing said second end;

d) a plurality of disks having cylindrical annular central segments interfitting with segments of an adjacent disk, interfitting of said disks forming a hollow, longitudinal passageway in an assembly of disks, said disks being formed with orifices and said assembly of disks and longitudinal passageway being located within said cylindrical reservoir, said longitudinal passageway being attached to said caps, e) an oxygen providing means attached to one end of said passageway to allow oxygen to be introduced centrally and axially into said hollow passageway wherein the oxygen is dispersed radially through the orifices; and f) a means for rotating said assembly of disks about its longitudinal axis.

9. The blood oxygenator of claim 8 wherein at least one of said caps is provided with blood level control means.

10. The blood oxygenator of claim 9 wherein said blood level control means is a horizontal slit formed near the bottom of said cap.

11. The blood oxygenator of claim 9, having, in addition, a blood reservoir annex in fluid connection with said blood level control means.

* * * * *